(12) United States Patent
Passarelli

(10) Patent No.: US 7,617,937 B1
(45) Date of Patent: Nov. 17, 2009

(54) EMERGENCY PERSONAL CHANGE KIT

(76) Inventor: William J. Passarelli, 1162 Audubon Dr., Toms River, NJ (US) 08753

( * ) Notice: Subject to any disclaimer, the term of this patent is extended or adjusted under 35 U.S.C. 154(b) by 427 days.

(21) Appl. No.: 11/715,762

(22) Filed: Mar. 8, 2007

(51) Int. Cl.
*A45C 15/00* (2006.01)
(52) U.S. Cl. ............... 206/581; 206/38; 206/823
(58) Field of Classification Search ............ 206/581, 206/225, 38, 235, 233, 37, 278, 823, 205, 206/210, 213
See application file for complete search history.

(56) References Cited

U.S. PATENT DOCUMENTS

| | | | |
|---|---|---|---|
| 4,702,378 A * | 10/1987 | Finkel et al. | 206/581 |
| 4,792,024 A * | 12/1988 | Morton et al. | 190/1 |
| 6,723,080 B1 | 4/2004 | Habib et al. | |
| 7,104,977 B2 | 9/2006 | Price et al. | |
| 2003/0136704 A1* | 7/2003 | Burgess | 206/581 |

* cited by examiner

*Primary Examiner*—Jacob K Ackun, Jr.
(74) *Attorney, Agent, or Firm*—Michael R. Philips

(57) ABSTRACT

An emergency personal change kit is provided for use after an accidental bowel episode. The kit includes disposable gloves, a safety cutter for removing a soiled undergarment, a plastic bag for disposal of soiled and used items, a wet cleansing wiper, a dry wiper, a hand sanitizer liquid, and a temporary, size-adjustable clean undergarment. The size-adjustable undergarment is at the large end of a size range and includes clips to secure the waistband in a comfortable size arrangement.

10 Claims, 2 Drawing Sheets

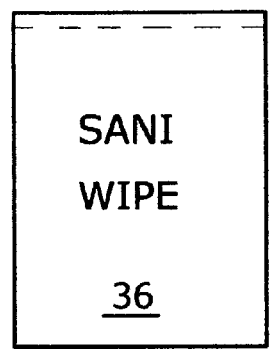 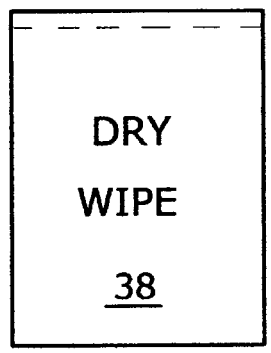 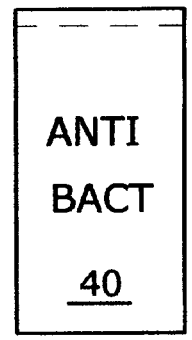
Fig. 6  Fig. 7
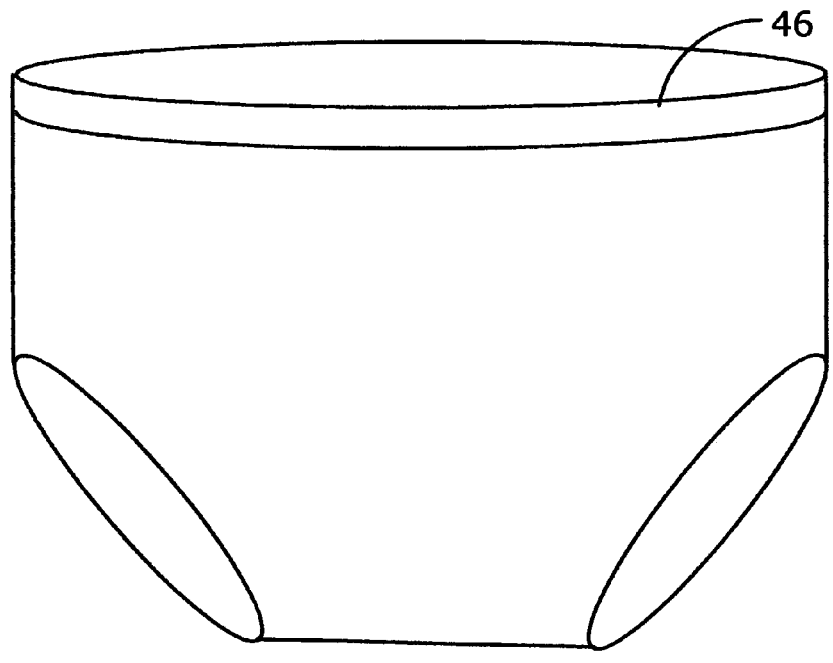 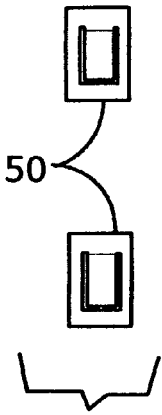
Fig. 8  Fig. 9

EMERGENCY PERSONAL CHANGE KIT

FIELD OF THE INVENTION

The present invention relates to the field of kits for personal hygiene and more particularly to kits for personal cleaning and garment changing in case of fecal matter soiling one's clothing.

BACKGROUND OF THE INVENTION

Most people experience accidental defecation occasionally. Some people, because of a high intestinal sensitivity or illness, experience bowel emergencies relatively often. Emergency or accidental defecation often does not happen in the vicinity of a bathroom, especially if one is traveling or working out-of-doors. If a bowel episode occurs in a location without accessible bathroom facilities, the likely result is the soiling of one's body and clothing. This result is unpleasant in odor and feel, embarrassing, may stain contact surfaces such as the seat of an automobile, and may ultimately spread infection.

After an accidental bowel episode occurs in an inconvenient location, the affected individual typically will go to the nearest private facility, perhaps a public bathroom or merely a hidden area to clean up as well as possible. The person must remove the outer garment and then remove the soiled undergarment, usually spreading the fecal matter to the hands and areas of the legs. Cleaning at best involves toilet paper and a sink, but may be much more rudimentary. Finally, redressing must be done without an undergarment since the soiled undergarment was necessarily disposed of, leaving the person fairly uncomfortable.

SUMMARY OF THE INVENTION

The present invention provides an emergency personal change kit to enable a greatly improved manner of eliminating the soiled undergarment, cleaning oneself and redressing with an adequate, but temporary, replacement undergarment. The kit contains a pair of disposable gloves and a cutter provided to remove the soiled undergarment. A sanitary wiping cloth and a dry wiping cloth are provided to deal with the fecal matter. An undergarment is included for temporary wear, and the person's outer garment is replaced. All soiled items are placed into a plastic bag for disposal. Finally, an antiseptic cleansing fluid is included to clean the hands.

BRIEF DESCRIPTION OF THE DRAWINGS

The present invention is best understood in conjunction with the accompanying drawing figures in which like elements are identified by similar reference numerals and wherein:

FIG. 6 is a front elevation view of a sanitary wiping cloth and a dry wiping cloth, each folded in a sealed packet.

FIG. 7 is a front elevation view of a sealed packet containing an anti-bacterial fluid for hand cleaning.

FIG. 8 is a front elevation view of a temporary replacement undergarment for use in the emergency personal change kit of the invention.

FIG. 9 is a front elevation view of a pair of mechanical clips used to adjust the undergarment shown in FIG. 8 to the waist size of the user.

DETAILED DESCRIPTION OF THE PREFERRED EMBODIMENT

Figure 1:
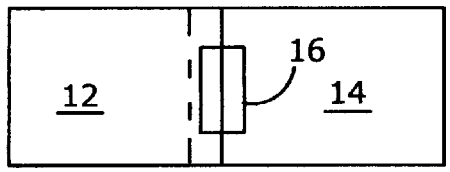
FIG. 1 is a side elevation view of a closed container for packaging the components comprising the emergency personal change kit of the invention.

Referring now to FIG. 1, a container 10 is shown in closed condition with a cover 12 snugly engaging a base 14. In the preferred embodiment of the invention, container 10 is formed as a right circular cylinder with flat ends. Optionally, a label or piece of adhesive tape 16 is positioned along the seam between cover 12 and base 14 to hold the parts together until container 10 is opened by a user. Other shapes may be used for alternate forms of container 10, for example an elliptical cylinder or a rectangular box. In addition, container 10 may be formed as flexible, e.g. a bag or envelope. Container 10, in any available shape, is sized to contain the several components of the present invention described below and is able to be placed in a pocket, purse or automobile glove compartment.

Figure 2:
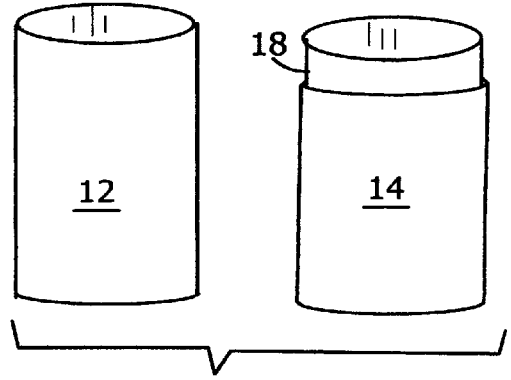
FIG. 2 is a side elevation view of the container of FIG. 1 in open condition with the two portions standing for ease of access.

In FIG. 2, container 10 is shown in the open condition with cover 12 and base 14 oriented vertically to present a pair of open top containers that rest securely on any convenient horizontal surface. Base 14 is formed with a rim 18 that is configured to slip into cover 12. Cover 12 and base 14 each are packed with several components of the invention kit, preferably with the components that are needed early in the process of cleaning positioned near the open tops of cover 12 and base 14. The following paragraphs describe the components of the invention kit in the typical order of use and method of use.

Figure 3:
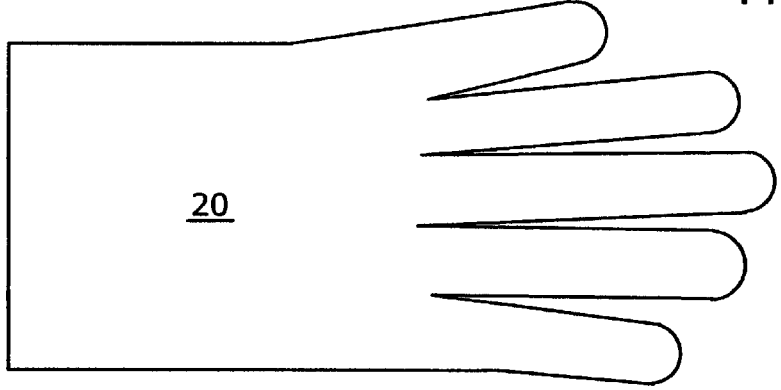
FIG. 3 is a side elevation view of a disposable glove for inclusion in the emergency personal change kit of the invention.

As described briefly above, the clean up of an accidental bowel episode is inherently messy. Referring now to FIG. 3, a disposable glove 20 is provided in the kit of the present invention. As the first needed article in the clean up process, glove 20 is packed near the intersection of cover 12 and base 14 to be readily accessible when container 10 is opened. Glove 20 is preferably an inexpensive plastic glove, e.g. vinyl, but may be any inexpensive, readily disposable, non-porous material that can be folded into a small bundle and stored for an extended period of time. Glove 20 is of the type and size to fit most hand sizes. Preferably, two gloves 20 are included for increased sanitary protection.

Figure 4:
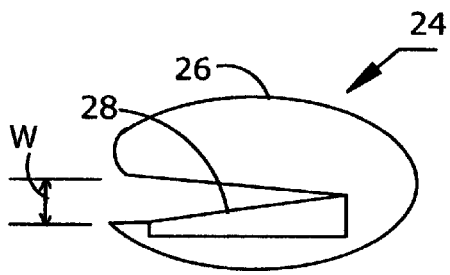
FIG. 4 is a side elevation view of a cutter of the emergency personal change kit of the invention.

Referring now to FIG. 4, a cutter 24 is illustrated in side view. Cutter 24 is of the type known as a safety letter opener that is typically shaped as an ellipse. A blade 28 is mounted, or insert molded, to reside in a wedge shaped opening below handle 26. The width W of the wedge shaped opening in handle 26 is less than the diameter of an adult finger to prevent injury from blade 28. Alternate shapes of cutter 24 are within the scope of the present invention, as long as width W of the wedge shaped opening is sufficiently small. Cutter 24 enables the user to cut and remove a soiled undergarment, thus minimizing the spread of fecal matter. Cutter 24 is sized to be packed in container 10 (see FIG. 1), and has a thickness in the direction perpendicular to the drawing on the order of 3.0 mm (⅛ inch).

Figure 5:
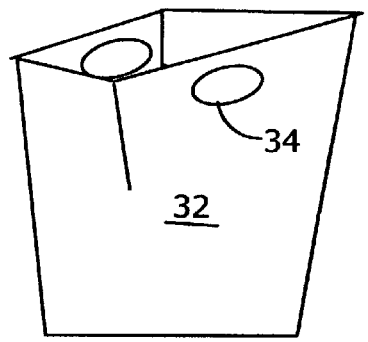
FIG. 5 is a receptacle in the form of a bag for receiving soiled items for disposal.

Referring now to FIG. 5, a receptacle 32 is shown in expanded condition. Receptacle 32 is preferably a disposable plastic bag, e.g. vinyl, to securely hold the soiled undergarment, cleaning components of the kit and excess fecal matter. Receptacle 32 is folded into a small bundle and stored in container 10 prior to use. Receptacle 32 is preferably formed with a pair of holes 34 to enable the user to hang receptacle 32 on a hook or other available structure, thus holding the bag open for easy insertion of waste matter. Optionally, a closure such as a twist tie band is enclosed.

Referring now to FIG. 6, a cleansing cloth or paper sheet that is pre-saturated with a cleansing liquid is provided in a sealed packet 36, identified in FIG. 6 as Sani Wipe. The enclosed sheet is of sufficient size when unfolded to enable cleaning of the soiled buttocks and thigh areas of the affected user. After using the moist cleansing cloth, a dry cloth or paper sheet is removed from a sealed packet 38 to dry the skin, identified in FIG. 6 as Dry Wipe. The dry sheet in Dry Wipe packet 38 is of similar size to the size of the moist sheet in Sani Wipe packet 36.

Referring now to FIG. 7, a packet 40, identified as Anti Bact, is retrieved from container 10 (see FIG. 1). Packet 40 contains a liquid anti-bacterial hand cleaner. Packets 36, 38 and 40 are formed with a perforated tear line to be easily opened for use. Alternatively, a liquid hand cleaner may be provided in a small bottle or tube. The liquid hand cleaner is of the type that does not require drying with a towel after use, one such liquid cleaner is known by the brand name Purel®.

Referring now to FIG. 8, a replacement undergarment 44 is provided for temporary use after cleaning has been accomplished. Undergarment 44 is preferably made of a thin, disposable, sheet material such as a non-woven fabric or paper, for reasons of economy and ease of folding. Due to the range of waist sizes that must be accommodated, undergarment 44 is provided in either a medium size, e.g. waist size 28 to 36 inches, or a large size, e.g. waist size 38 to 50 inches. The waistband 46 of undergarment 44 is able to be folded to adjust to the waist size of the wearer, and a pair of clips 50, illustrated in FIG. 9, is provided. Clips 50 are either molded plastic or metal, and are resilient to hold snugly onto waistband 46. Alternate closure devices, for example hook-and-loop type fasteners, are considered within the scope of the invention.

Use of the invention emergency personal change kit generally follows the steps outlined below:

1. Remove tape or label 16, open container 10, and place cover 12 and base 14 on a supporting surface (see FIGS. 1, 2);
2. Remove, unfold, and put glove(s) 20 on the hand(s) (see FIG. 3);
3. Remove, unfold, and place in an accessible position receptacle 32 (see FIG. 5);
4. Remove, or place in a safe position, the user's outer garment, e.g. pants or skirt;
5. Remove cutter 24 (see FIG. 4) from container 10; cut the soiled undergarment from the waist to the leg opening of each side and remove the undergarment; place the soiled undergarment and cutter 24 in receptacle 32;
6. Remove the cleanser-saturated cloth from Sani Wipe packet 36 (see FIG. 6) and place the empty packet in receptacle 32;
7. Unfold the cleanser-saturated cloth and clean the fecal residue from the buttocks and thighs; place the used cleaning cloth in receptacle 32;
8. Remove the dry cloth from Dry Wipe packet 38 (see FIG. 6) and place the empty packet in receptacle 32;
9. Unfold the dry cloth and dry the areas that are wet from cleaning; place the used dry cloth in receptacle 32;
10. Remove glove(s) 20 from the hand(s) and place in receptacle 32;
11. Open the Anti Bact packet 40 (see FIG. 7), dispense the anti-bacterial liquid hand cleaner to clean the hands; place the empty packet in receptacle 32;
12. Remove replacement undergarment 44 (see FIG. 8) from container 10; don undergarment 44; adjust waistband 46 of undergarment 44 to fit user;
13. Remove clips 50 (see FIG. 9) from container 10; apply one or both clips to folded waistband 46 to hold undergarment 44 in place;
14. Reposition the outer garment, e.g. pants or skirt;
15. Close and dispose of receptacle 32.

Whereas the kit of the invention disclosed is intended for emergency use, it is understood that the user will conduct a more thorough cleaning and acquire clean clothing items as needed. However, the kit invention avoids the need for the person to continue to endure fecal matter on the body, wear soiled clothing, and the unpleasant odor associated therewith.

While the description above discloses preferred embodiments of the present invention, it is contemplated that numerous variations and modifications of the invention are possible and are considered to be within the scope of the claims that follow.

What is claimed is:

1. An emergency personal change kit, comprising:
   a. means for protecting the hand of a person while removing soiled clothing items after an accidental bowel episode;
   b. means for removing the soiled clothing items from the person with a minimal spread of fecal matter;
   c. a receptacle for disposal of soiled clothing items and used components of the emergency personal change kit;
   d. means for cleaning body parts and hands of the person;
   e. a temporary replacement clean clothing item; and
   f. wherein the components of the emergency personal change kit are contained in a package.

2. The emergency personal change kit described in claim 1, wherein the means for protecting the hand of a person comprises a disposable glove.

3. The emergency personal change kit described in claim 1, wherein the means for removing the soiled clothing items from the person comprises a cutter.

4. The emergency personal change kit described in claim 3, wherein the cutter is configured with a blade mounted in a protected manner to minimize the chance of injury.

5. The emergency personal change kit described in claim 1, wherein the receptacle comprises a disposable bag.

6. The emergency personal change kit described in claim 1, wherein the means for cleaning body parts and hands comprises a packaged cloth saturated with a cleansing solution.

7. The emergency personal change kit described in claim 6, wherein the means for cleaning body parts and hands further comprises a packaged dry cloth.

8. The emergency personal change kit described in claim 6, wherein the means for cleaning body parts and hands further comprises a packaged anti-bacterial fluid.

9. The emergency personal change kit described in claim 1, wherein the temporary replacement clean clothing item includes means for adjusting the waist size thereof to accommodate the person.

10. The emergency personal change kit described in claim 9, wherein the means for adjusting the waist size comprises one or more clips adapted for snugly holding portions of a waistband of the garment.

* * * * *